(12) United States Patent
Lampert

(10) Patent No.: US 7,121,827 B2
(45) Date of Patent: Oct. 17, 2006

(54) ENDODONTIC INSTRUMENT

(76) Inventor: Christopher Lampert, 712 Lake Forest Dr., Lake Oswego, OR (US) 97034

( * ) Notice: Subject to any disclaimer, the term of this patent is extended or adjusted under 35 U.S.C. 154(b) by 42 days.

(21) Appl. No.: 10/899,658

(22) Filed: Jul. 26, 2004

(65) Prior Publication Data

US 2005/0003326 A1   Jan. 6, 2005

Related U.S. Application Data

(63) Continuation of application No. PCT/US03/02072, filed on Jan. 22, 2003.

(60) Provisional application No. 60/411,641, filed on Sep. 18, 2002, provisional application No. 60/387,214, filed on Jun. 10, 2002, provisional application No. 60/352,610, filed on Jan. 28, 2002.

(51) Int. Cl.
    *A61C 5/02*   (2006.01)
(52) U.S. Cl. .......................................... 433/72; 433/102
(58) Field of Classification Search ................. 433/27, 433/32, 72, 75, 102; 600/589, 590
    See application file for complete search history.

(56) References Cited

U.S. PATENT DOCUMENTS

| | | | | |
|---|---|---|---|---|
| 1,943,543 A * | 1/1934 | McFadden | ................... | 606/49 |
| 3,753,434 A * | 8/1973 | Pike et al. | ..................... | 433/32 |
| 3,916,529 A | 11/1975 | Mousseau | | |
| 4,025,964 A * | 5/1977 | Owens | .................... | 623/11.11 |
| 4,193,408 A | 3/1980 | Fujino | | |
| 4,211,456 A * | 7/1980 | Sears | ........................... | 439/39 |
| 4,260,379 A | 4/1981 | Groves et al. | | |
| 4,268,251 A | 5/1981 | Tagasugi et al. | | |
| 4,332,561 A | 6/1982 | McSpadden | | |
| 4,362,166 A * | 12/1982 | Furler et al. | ................ | 600/483 |
| 4,568,281 A | 2/1986 | Harvey et al. | | |
| 4,653,503 A * | 3/1987 | Heath | ......................... | 600/391 |
| 4,824,369 A | 4/1989 | Levy | | |
| 4,836,780 A | 6/1989 | Buchanan | | |
| 5,112,224 A | 5/1992 | Shirota | | |
| 5,213,499 A | 5/1993 | Levy | | |
| 5,421,727 A * | 6/1995 | Stevens et al. | ............. | 433/224 |
| 5,775,903 A | 7/1998 | Atkins | | |
| 6,331,111 B1 * | 12/2001 | Cao | ........................... | 433/29 |
| 6,520,773 B1 | 2/2003 | Weber | | |
| 6,712,813 B1 * | 3/2004 | Ellman et al. | ................ | 606/41 |
| 6,872,075 B1 * | 3/2005 | Regan | ........................ | 433/102 |

OTHER PUBLICATIONS

International Search Report for International Application No. PCT/US03/02072, dated Jul. 1, 2003; 4 pages.
International Written Opinion for International Application No. PCT/US03/02072, dated Aug. 20, 2004; 4 pages.
International Search Report for International Application No. PCT/US03/02072, dated May 31, 2005; 4 pages.

* cited by examiner

Primary Examiner—Ralph A. Lewis
(74) Attorney, Agent, or Firm—Ganz Law, P.C.

(57) ABSTRACT

An endodontic instrument for root canal treatment is provided having a working portion manipulated by a handle and a connection assembly for attachment with an electronic apex locator. The connection assembly allows the electronic apex locator to be connected to the instrument at or through the coronal end of the handle. Preferably, the connection assembly includes a male/female assembly located within or on the surface the file handle.

5 Claims, 6 Drawing Sheets

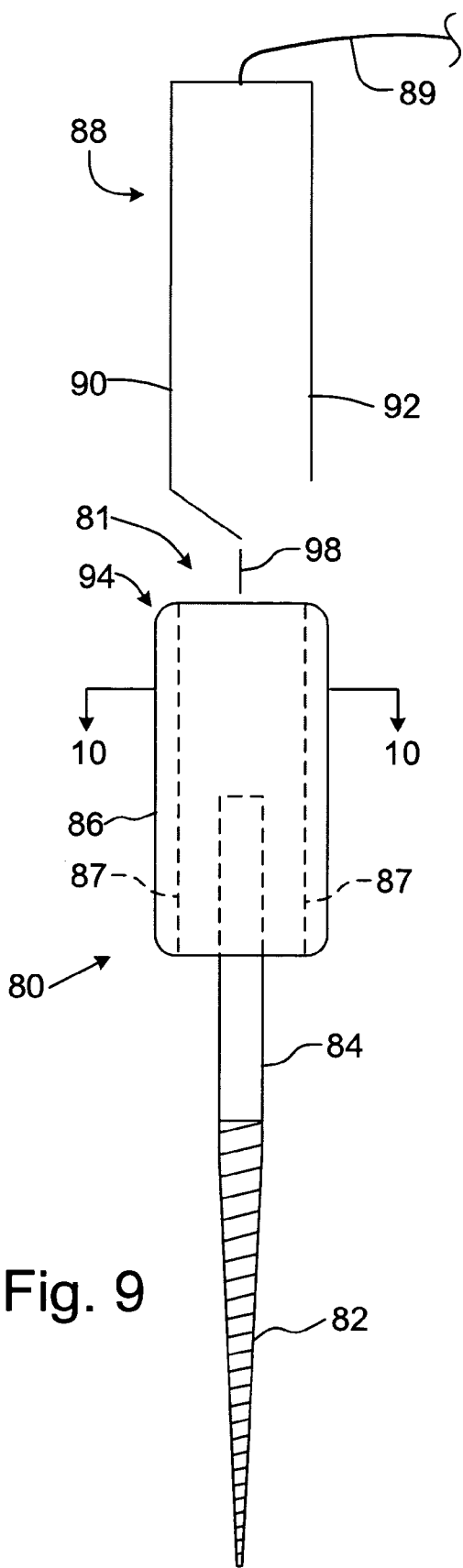
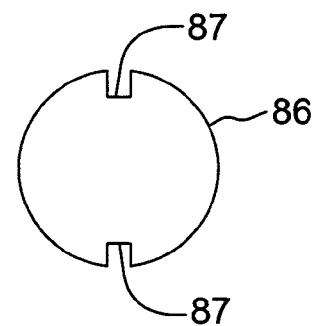
Fig. 9
Fig. 10

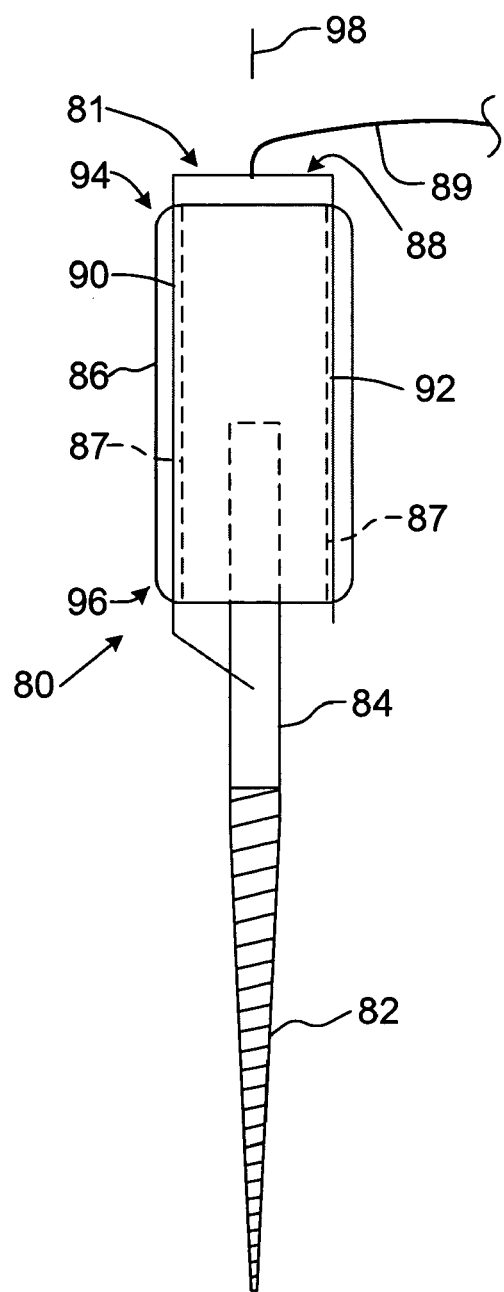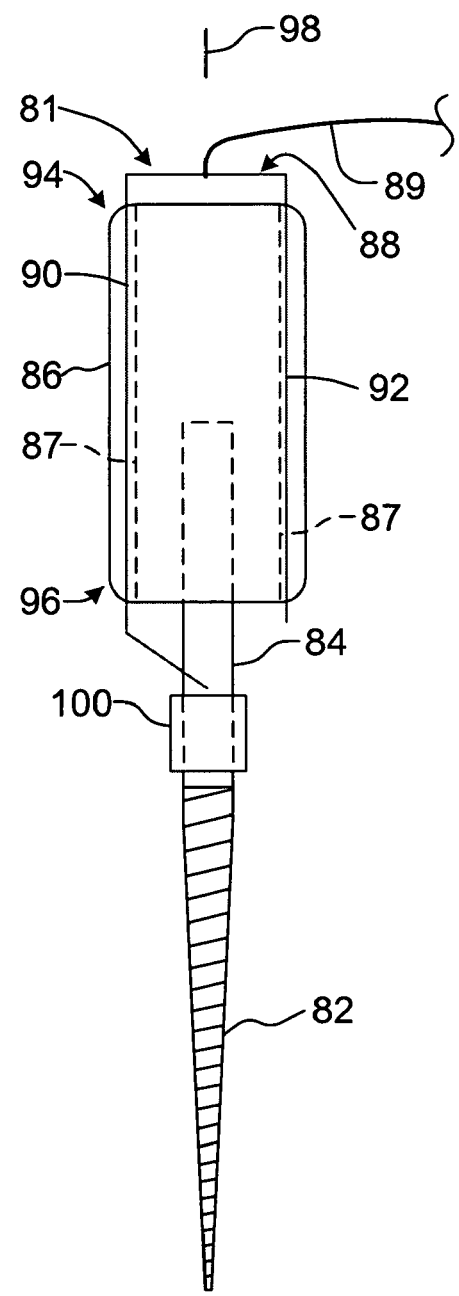

ENDODONTIC INSTRUMENT

CROSS-REFERENCE TO RELATED APPLICATIONS

This application is a continuation of International PCT application No. PCT/US2003/02072, filed Jan. 22, 2003, which claims priority to and the benefit of U.S. Provisional Patent Application Ser. Nos. 60/352,610, filed Jan. 28, 2002; 60/387,214, filed Jun. 10, 2002; and 60/411,641, filed Sep. 18, 2002, the entire disclosures of which are hereby incorporated by reference as if recited in full herein for all purposes.

FIELD OF THE INVENTION

This invention relates generally to endodontic instruments for performing root canal procedures and, more particularly, to a connection assembly for electrically connecting an endodontic file to an electronic apex locator.

BACKGROUND OF THE INVENTION

Traditional endodontic files consist of a tapered cutting flute portion having a shaft connected to a handle that is gripped by a user such as, for example, a dentist or an endodontist. Endodontic files are used to remove the contents of a root canal and to prepare and/or shape the root canal prior to filling it. Endodontic files are also used to determine the length of the root canal by connecting an electronic apex locator to the endodontic file. An electronic apex locator is an electronic measuring device used to determine the length of root canals.

FIG. 1 shows a traditional endodontic file 10 with tapered cutting flutes 12 located at one end of a shaft 14 secured to a handle 16 that is grasped by a user to perform the root canal procedure. Typically, shaft 14 is connected to an apical end 18 of handle 16 and the user grasps handle 16 to perform the root canal procedure.

As seen in FIG. 2, an electronic apex locator (not shown) is connected to the endodontic file 10 by an electrically conductive clip or other mechanism 22 attached to shaft 14 between tapered cutting flutes 12 and handle 16 in order to measure the length of the root canal. Clip 22 is connected to the apex locator by an electrically conductive wire 23 and tapered cutting flutes 12 and shaft portion 14 are made of an electrically conductive material so that electrical signals can be sent from tapered cutting flutes 12 to the apex locator. One problem of the assembly shown in FIG. 2 is that clip 22 is typically attached to shaft 14 between tapered cutting flutes 12 and handle 16 forming a 90° angle lever on shaft 14.

This location of attachment of clip 22 to shaft 14 is undesirable because it impairs visibility. Additionally, unwanted lateral forces may be imparted to shaft 14. Such forces impair the dexterity of file manipulation and impair the angle of file insertion into the root canal. Furthermore, attaching the electronic apex locator to shaft 14 prevents the use of an electrical insulating sheath on shaft 14.

Endodontic instruments are also shown in described in U.S. Pat. No. 4,260,379 (Groves et al.), U.S. Pat. No. 4,332,561 (McSpadden), U.S. Pat. No. 4,824,369 (Levy), U.S. Pat. No. 5,112,224 (Shirota), U.S. Pat. No. 5,213,499 (Levy), and U.S. Pat. No. 5,775,903 (Atkins), and Buchanan (U.S. Pat. No. 4,836,780), the entire disclosures of which patents are hereby incorporated by reference as if set forth in their entirety for all purposes.

SUMMARY OF THE INVENTION

The present invention provides an endodontic file that overcomes difficulties associated with prior endodontic instruments. Specifically, the present invention provides an endodontic file having an improved connection assembly with an electronic apex locator.

In a first embodiment, the endodontic file of the present invention includes a connection assembly for an electronic apex locator wherein the connection is made at the coronal end of the file handle opposite the tapered cutting flutes. The file shaft extends through the handle so that a portion of the file shaft extends out of the coronal end of the handle. A clip or other mechanism is attached to the exposed shaft end to connect the electronic apex locator to the file. This connection assembly improves visibility and file manipulation.

In another embodiment, the endodontic file includes a connection assembly for an electronic apex locator wherein the connection is made within the handle. The assembly includes a male component and a female component connected together by a plug-in assembly. The female component includes a recess or central opening within the file handle. The male component includes at least one electrically conductive pin having an electrical wire lead connected to the electronic apex locator. During use, the male component is inserted into the female component so that an electrical connection is formed between the electronic apex locator and the endodontic file.

In yet another embodiment, the endodontic file includes a connection assembly for an electronic apex locator wherein the connection is made on and along the length of the handle. The connection assembly includes a male clip attached to and extending along the length of the handle. The clip is made of an electrically conductive material and has an electrical wire lead connected to the electronic apex locator. The handle includes female slots or recesses extending along the length of the handle that receive the clip during use so that the clip makes electrical contact with the file shaft.

In still another embodiment, the endodontic file includes a file shaft insulator located on the file shaft between the handle and the tapered cutting flutes for preventing an electrical short during use on a tooth with a metallic restoration.

The electronic apex locator connection assembly of this invention improves dexterity of file manipulation, improves visibility, improves tactile feedback, allows the electronic apex locator to be attached to the file at multiple angles, allows for the use of a file shaft insulator, and eliminates the use of a large traditional apex locator connection clip which creates a lever on the file shaft. These improvements make root canal procedures more accurate and efficient for both the practitioner and the patient.

These and other embodiments are described in more detail in the following description of the drawings and detailed description of the invention.

BRIEF DESCRIPTION OF THE DRAWINGS

FIG. 8 is a view similar to FIG. 6 showing a shaft insulator sheath.

FIG. 9 is an exploded view of another embodiment of a connection assembly for an endodontic instrument and an electronic apex locator FIG. 10 is a sectional view of the handle taken along lines 10—10 in FIG. 9.

FIG. 11 is an assembly view of the embodiment of FIG. 9.

FIG. 12 is a view similar to FIG. 11 showing a shaft insulator.

DETAILED DESCRIPTION OF THE INVENTION

Figure 1:
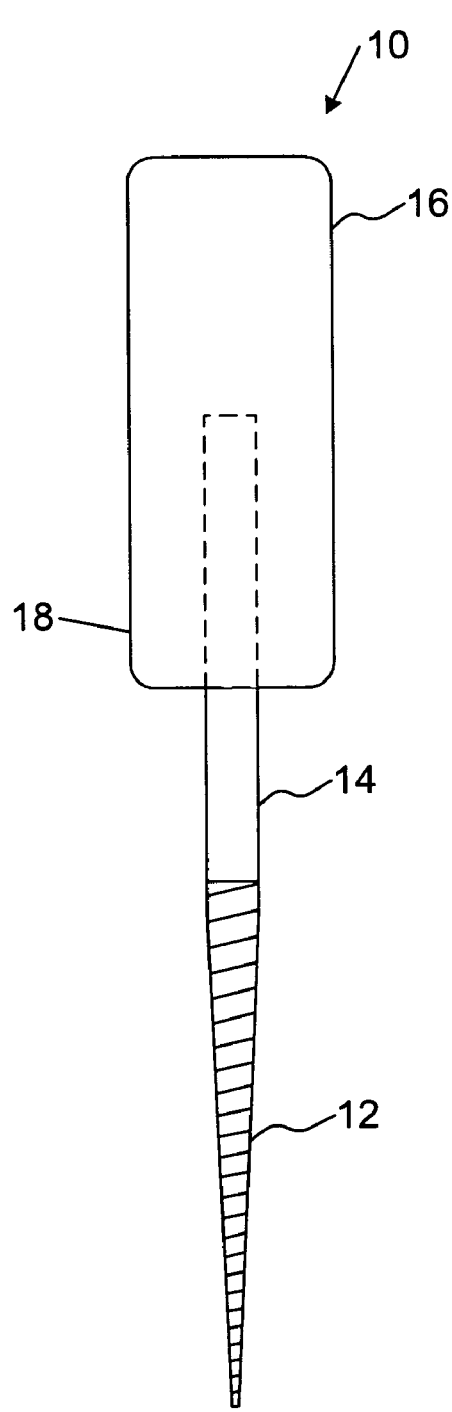
FIG. 1 is an illustration showing a traditional prior art endodontic instrument.
Figure 2:
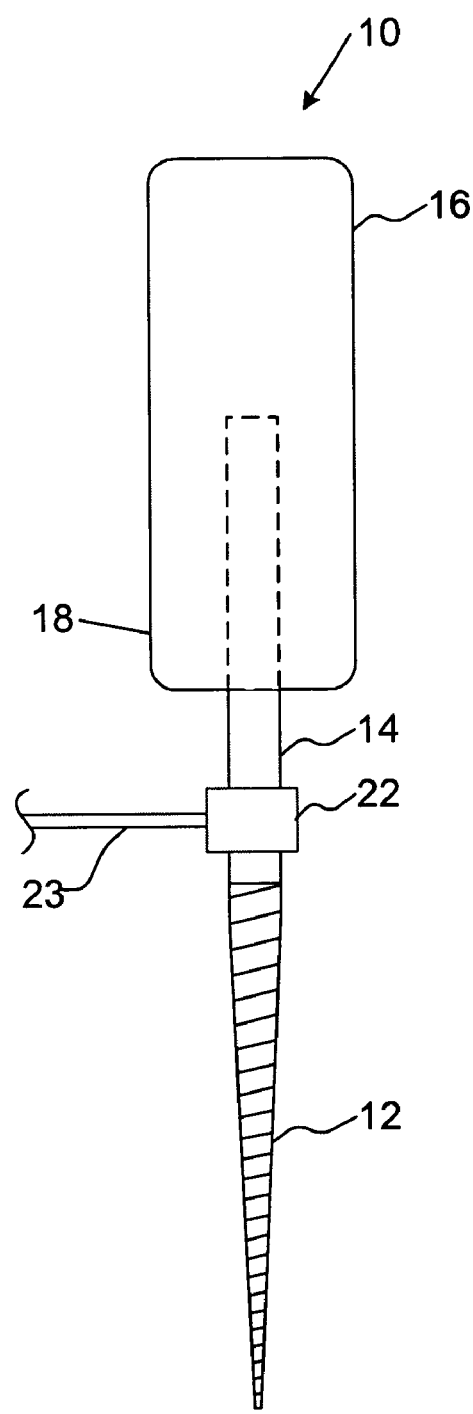
FIG. 2 is an illustration similar to FIG. 1 showing a traditional prior art electronic apex locator attached to the endodontic instrument.
Figure 3:
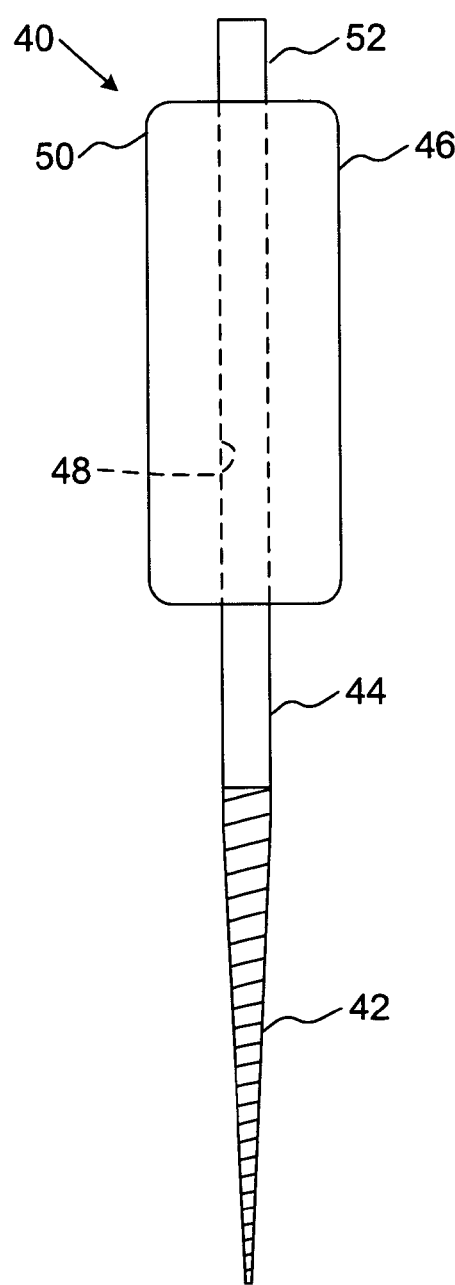
FIG. 3 is a view of a first embodiment of an endodontic instrument.
Figure 4:
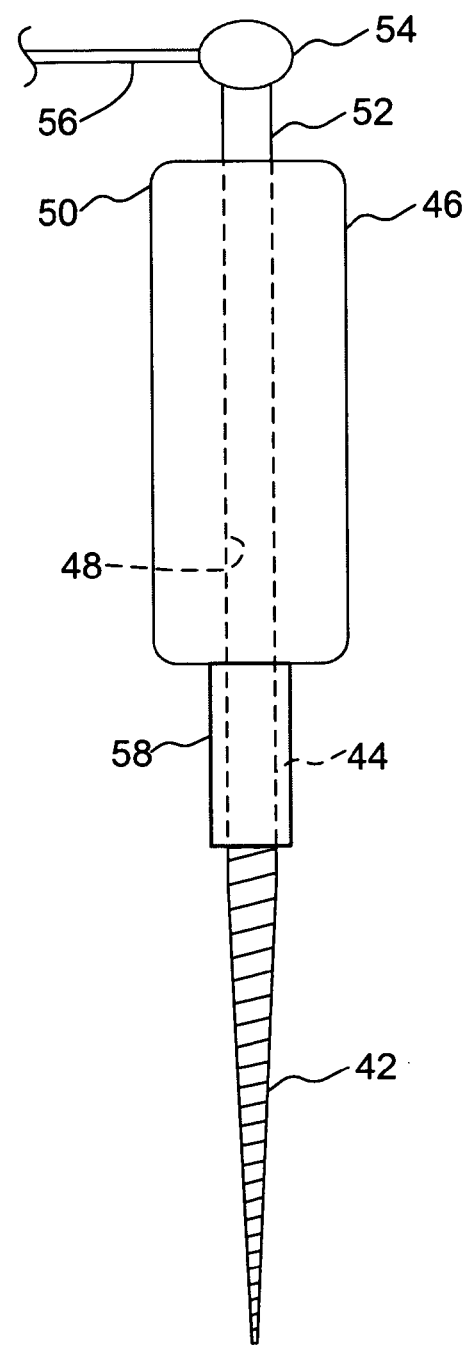
FIG. 4 is a view of the endodontic instrument of FIG. 3 with a connection assembly for an electronic apex locator.

A first embodiment of an endodontic file of the present invention is shown in FIGS. 3 and 4 having a connection assembly for an endodontic file and an electronic apex locator wherein the connection is made at one end of the file handle. Endodontic file 40 is shown as an elongate element having tapered cutting flutes 42 comprising a working end for insertion into a root canal (not shown) and a shaft 44 secured to a handle 46 to be grasped by a user. Shaft 44 is secured by any convenient means to handle 46. Preferably, shaft 44 extends through and is held within a central opening 48 in handle 46. As seen most clearly in FIG. 3, shaft 44 extends past a coronal end 50 of handle 46 resulting in an exposed portion 52 to which the electronic apex locator is attached.

As shown in FIG. 4, exposed portion 52 provides a connection site for a connector 54 for an electronic apex locator. Connector 54 includes a conductor such as, for example, an electrical wire 56 as best seen in FIG. 4 for connection with the electronic apex locator. Connector 54 may be any type of fastener that securely attaches to exposed portion 52 of shaft 44. For example, connector 54 may comprise a spring clip, clasp, or any fastening device that provides a mechanical attachment. Alternatively, connector 54 may comprise a pin, wire, or other component that is attached to exposed portion 52 by soldering or other similar methods. Thus, any type of connector may be used to establish an electrical connection at the attachment site of exposed portion 52 and connector 54. In use, connector 54 is attached to exposed portion 52 so that electrical signals are transmitted from tapered cutting flutes 42 to the apex locator to report conditions such as, for example, the depth of the cutting flutes 42 within the root canal.

Although FIGS. 3 and 4 show shaft 44 extending completely through handle 46 for attachment with the electronic apex locator it is understood that other electrical connections may be formed. For example, the end of shaft 44 may be located within handle 46 with an electrically conductive element secured thereto and extending past coronal end 50 of handle 46 for attachment to connector 54. As another example as seen in FIG. 5, the end of shaft 44 may be located within handle 46 with a portion of the middle of handle 46 removed to form a window 47 in handle 46 to expose shaft 44 to allow for attachment to connector 54.

An optional electrical insulating sheath 58 (FIG. 4) may be provided on shaft 44 between handle 46 and tapered cutting flutes 42 to prevent electrical shorting that may occur when, for example, the instrument is in use with a tooth having a metallic restoration.

FIGS. 5–11 show embodiments in which the endodontic instrument includes a connection assembly for the electronic apex locator that extends along an axis coincident with or substantially parallel to a central longitudinal axis of the endodontic instrument. The connection assembly is advantageous because it does not obstruct the view of the root canal and also eliminates any unnecessary lateral forces that may be caused by the 90° lever-type attachment of FIG. 4. Additionally, the embodiments of FIGS. 5–11 may be manipulated either by hand or rotationally driven by a motorized device such as, for example, a dental drill (not shown).

Figure 5:
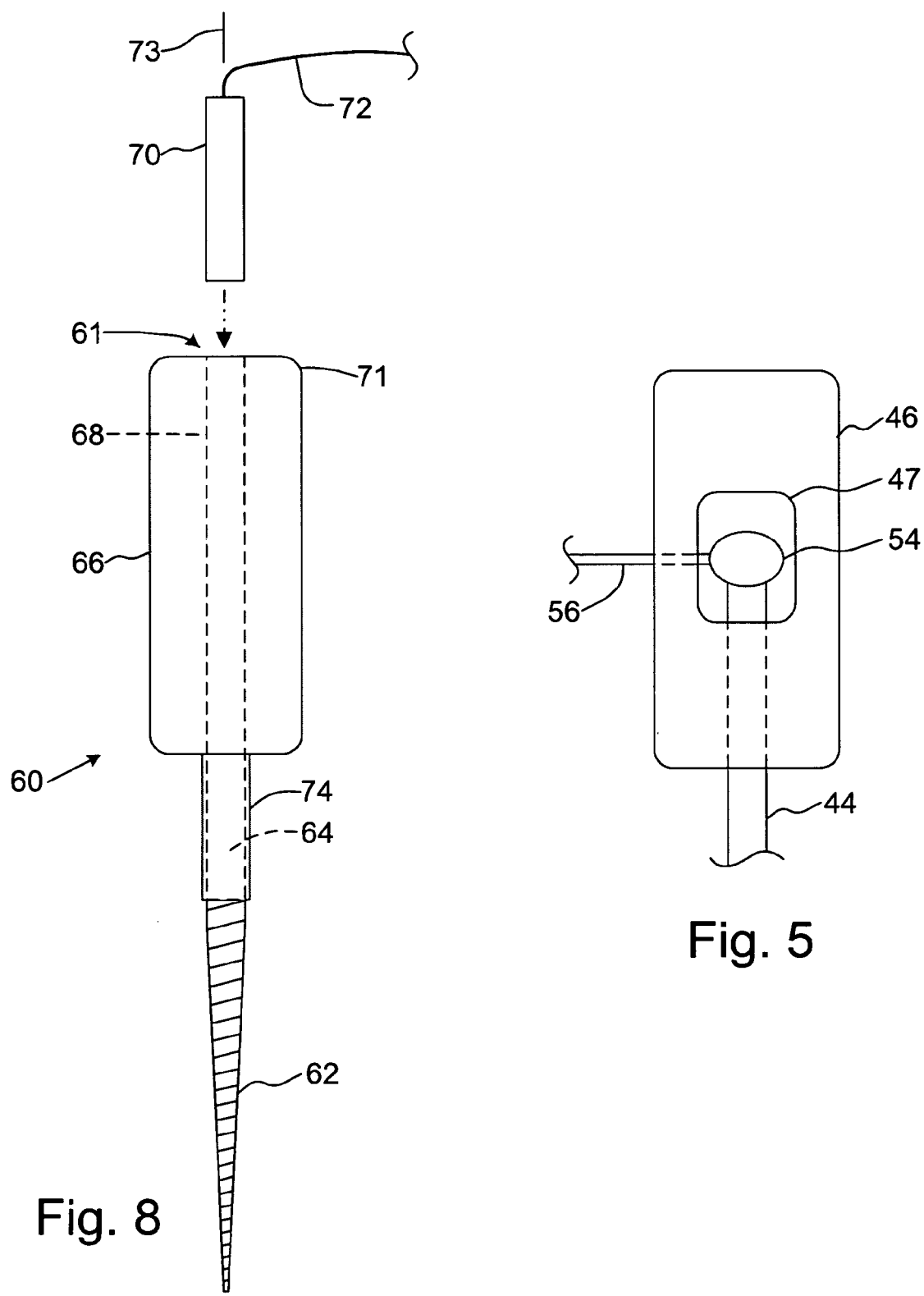
FIG. 5 is a partial view of the instrument handle having an access window for attachment of an electronic apex locator.
Figure 6:
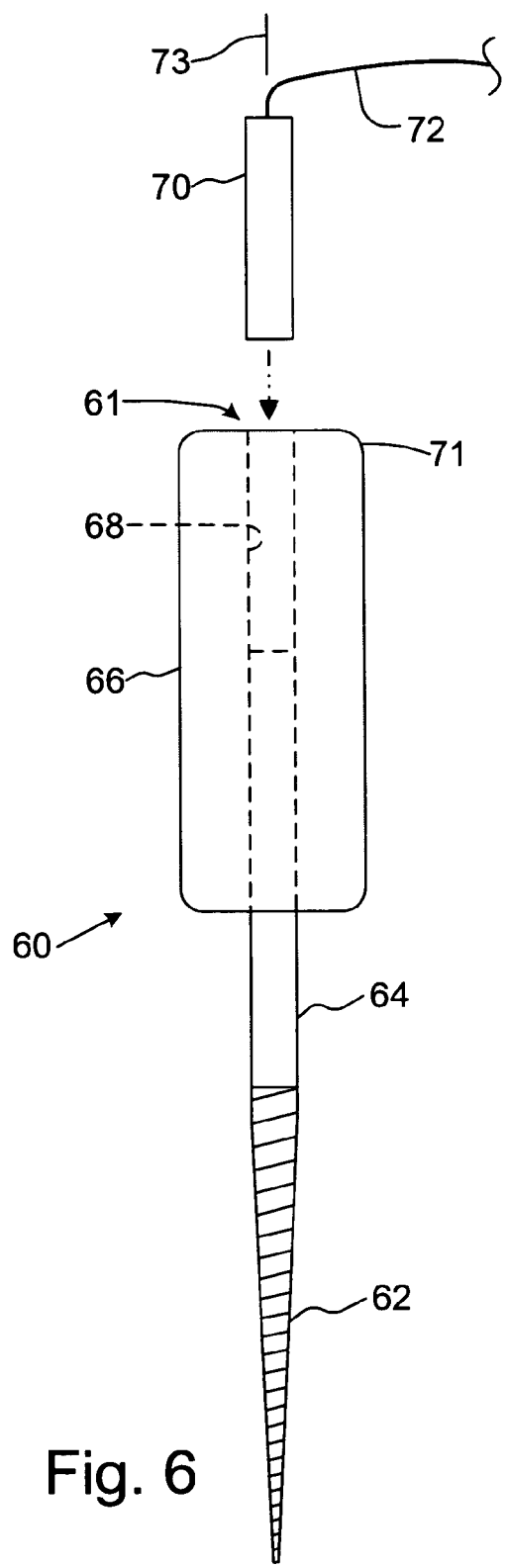
FIG. 6 is an exploded view of another embodiment of a connection assembly for an endodontic file and an electronic apex locator.
Figure 7:
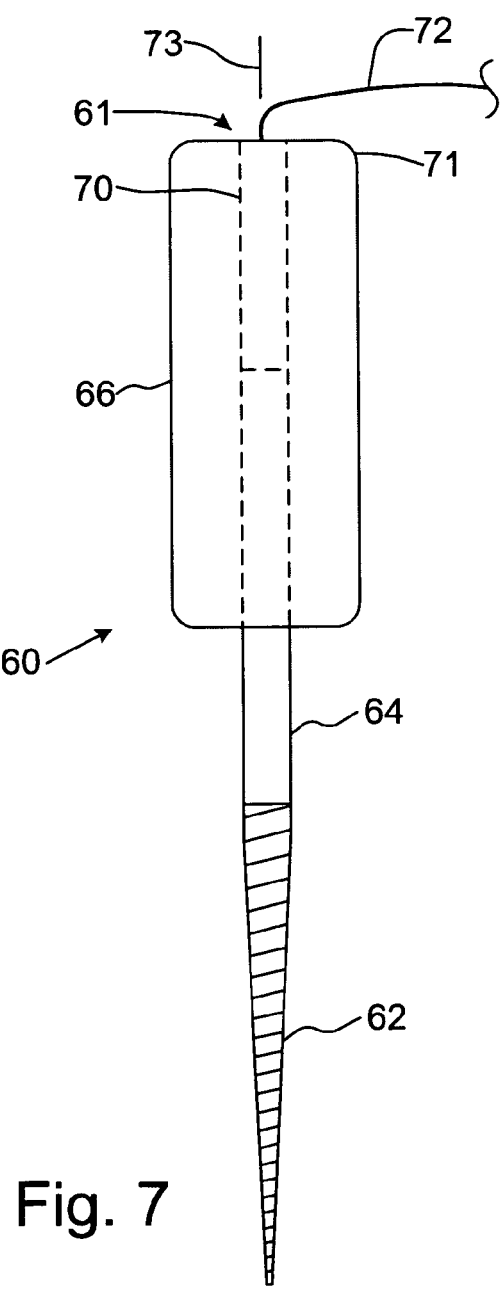
FIG. 7 is an assembly view of the embodiment of FIG. 6.

More specifically, FIGS. 5–7 show an endodontic file 60 in which a connection assembly 61 between endodontic file 60 and an electronic apex locator (not shown) is in the form of a male/female plug-in connection. Tapered cutting flutes 62 have a shaft 64 at one end securely received and held within handle 66. Handle 66 includes a central opening 68 to receive a male connector pin 70 electrically connected to the electronic apex locator by wire 72 or other conductor. Pin 70 is made of an electrically conductive material so that an electrical connection can be made with shaft 64. In use, pin 70 is inserted into opening 68 as seen in FIG. 6 so that pin 70 makes electrical contact with the end of shaft 64. Pin 70 is held in place by frictional engagement with walls of opening 68. This connection allows electrical signals to be transmitted from tapered cutting flutes 62 to the electronic apex locator. As can be seen, pin 70 is inserted into opening 68 at the coronal end 71 of handle 66 so that connection assembly 61 extends substantially along a central longitudinal axis 73 of endodontic file 60.

Additionally, shaft portion 64 and pin 70 may be held together magnetically. For example, one of either shaft portion 64 or pin 70 may be made of a magnetic material or may include a magnetized portion to magnetically hold the other of shaft portion 64 or pin 70.

FIG. 7 shows an optional electrical insulating sheath 74 provided on shaft portion 64 between handle 66 and tapered cutting flutes 62 to prevent electrical shorting, for example, when in use with a tooth having a metallic restoration.

FIGS. 8–10 show a preferred embodiment of an endodontic file 80 in which a connection assembly 81 for an electronic apex locator is located within or on the surface of the file handle. More specifically, endodontic file 80 includes tapered cutting flutes 82 with a shaft 84 securely received and held within a handle 86. Connection assembly 81 is in the form of a male/female connection in which the female component includes recessed grooves 87 on opposing sides of handle 86. The male component is preferably in the form of a clip 88 having opposed legs 90 and 92 to be inserted over coronal end 94 of handle 86 so that, during use, legs 90 and 92 are received in grooves 87. As seen in FIGS. 8 and 10, connection assembly 81 extends substantially along a central longitudinal axis 98 of endodontic file 80.

Although FIGS. 8–10 show the female component of connection assembly 81 as being grooves 87 along an outer surface of handle 86 it is understood that the female component may be in other forms. For example, the female component of connection assembly 81 may include opposed openings or holes extending completely through handle 86 to receive legs 90 and 92 of clip 88.

Clip 88 includes an electric wire 89 or other conductor for electrical connection to the apex locator (not shown). Wire 89 is permanently attached by any method such as, for example, by soldering. At least a portion of clip 88 must make contact with shaft 84 to provide an electrical connection therebetween so that electrical signals can be transmitted from tapered cutting flutes 82 to the apex locator.

As seen most clearly in FIG. 10, one of the opposed legs (shown as leg 90) of clip 88 extends through apical end 96 of handle 86 and extends toward axis 98 to make contact with shaft 84. Although the contact point between clip 88 and shaft 84 is shown below apical end 96 of handle 86 it is understood that clip 88 may contact shaft 84 at other locations such as, for example, within handle 86.

An optional electrical insulating sheath 100, shown in FIG. 11, prevents the instrument from forming a short electrical circuit when using an electronic apex locator on a tooth with a metallic restoration.

Although the embodiments of the present invention are shown and described as being related to endodontic instruments for measuring the length of a root canal, it is understood that this invention contemplates other uses such as, for example, measuring and/or sensing other conditions at a surgical site. This may be accomplished by utilizing an electronic or other type of sensor located in or on the endodontic instrument that receives and/or sends electronic or other signals to a monitoring device through a connection assembly as disclosed herein.

The present invention greatly improves the use of an endodontic file with an electronic apex locator by an improved connection therebetween. The improved connection assembly between the endodontic file and electronic apex locator allows for greater dexterity when manipulating the file, provides improved visibility of the root canal and file, allows the electronic apex locator to be attached to the file at multiple locations, and provides for a more accurate measurement of the root canal. Additionally, the present invention improves the use of the endodontic file with an electronic apex locator by improving tactile feedback, decreasing the weight of the connection assembly and eliminating the application of unnecessary lateral forces. The present invention further reduces the risk of an electrical short by providing an electrical insulator sheath.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

The invention claimed is:

1. An endodontic instrument used in performing a root canal treatment, comprising:
    an element extending along an axis having a working portion for insertion into the root canal of a tooth and a handle to be grasped by a user, and
    a male or female connection assembly for an electronic apex locator, the connection assembly being located on the handle so that electronic signals can be transmitted from the working portion to the electronic apex locator, wherein the connection assembly includes a magnetized portion.

2. An endodontic instrument used in performing a root canal treatment, comprising:
    an element extending along an axis having a working portion for insertion into the root canal of a tooth and a handle to be grasped by a user, and
    a male or female connection assembly for an electronic apex locator, the connection assembly being located on the handle so that electronic signals can be transmitted from the working portion to the electronic apex locator, wherein the connection assembly extends within a plane substantially coincident with or parallel to the axis, and wherein the female portion comprises substantially opposed openings in the handle to receive the male portion.

3. The endodontic instrument of claim 2, wherein the working portion of the element includes tapered cutting flutes having a shaft connected to the handle, the male portion comprising a clip having opposed legs in which at least one of the opposed legs contacts the shaft.

4. An endodontic instrument used in performing a root canal treatment, comprising:
    an element extending along an axis having a working portion for insertion into the root canal of a tooth and a handle to be grasped by a user, and
    a male or female connection assembly for an electronic apex locator, the connection assembly being located on the handle so that electronic signals can be transmitted from the working portion to the electronic apex locator, wherein the connection assembly extends within a plane substantially coincident with or parallel to the axis, and, wherein the female portion comprises opposed grooves on an outer surface of the handle to receive the male portion.

5. The endodontic instrument of claim 4, wherein the working portion of the element includes tapered cutting flutes having a shaft connected to the handle, the male portion comprising a clip having opposed legs received in the opposed grooves in which at least one of the opposed legs contacts the shaft.

* * * * *